United States Patent [19]

Shimizu et al.

[11] Patent Number: 4,814,494

[45] Date of Patent: * Mar. 21, 1989

[54] METHOD FOR PRODUCING (ARYL SUBSTITUTED) CARBOXYLIC ACID OR ITS SALT

[75] Inventors: Isoo Shimizu; Yasuo Matsumura, both of Yokohama; Yoshihisa Inomata, Kawasaki, all of Japan

[73] Assignee: Nippon Petrochemicals Company, Ltd., Tokyo, Japan

[ * ] Notice: The portion of the term of this patent subsequent to Nov. 24, 2004 has been disclaimed.

[21] Appl. No.: 11,735

[22] Filed: Feb. 6, 1987

[30] Foreign Application Priority Data

Feb. 8, 1986 [JP] Japan .................................. 61-26247

[51] Int. Cl.$^4$ ............................................. C07C 51/29
[52] U.S. Cl. .................... 562/419; 562/460; 562/465; 562/466; 562/490; 562/494
[58] Field of Search ............... 562/419, 494, 460, 465, 562/466, 490

[56] References Cited

U.S. PATENT DOCUMENTS

| 4,694,100 | 9/1987 | Shimizu | 562/419 |
| 4,709,089 | 11/1987 | Shimizu | 562/494 |

FOREIGN PATENT DOCUMENTS

| 53-18534 | 2/1978 | Japan | 562/419 |
| 53-149962 | 12/1978 | Japan | 562/419 |
| 61-65838 | 4/1986 | Japan | 562/419 |
| 61-65839 | 4/1986 | Japan | 562/419 |

*Primary Examiner*—Michael L. Shippen
*Attorney, Agent, or Firm*—Scully, Scott, Murphy & Presser

[57] ABSTRACT

An effective method for producing highly pure (aryl substituted)carboxylic acid or its salt which comprises the steps of:

(I) oxidizing (aryl substituted)aldehyde in an acidic phase in the presence of hypohalogenite; and (II) bringing the oxidized product obtained in the preceding step into contact in a liquid phase with hydrogen in the presence of a catalyst of transistion metal of the group VIII in the periodic table.

14 Claims, No Drawings

METHOD FOR PRODUCING (ARYL SUBSTITUTED) CARBOXYLIC ACID OR ITS SALT

BACKGROUND OF THE INVENTION (1) Field of the Invention

This invention relates to a method for producing (aryl substituted)carboxylic acid or its salt which is useful as a medicine or an intermediate for preparing organic chemicals such as medicines. More particularly, this invention relates to a method for producing highly pure (aryl substituted)carboxylic acid or its salt in which (aryl substituted)aldehyde is oxidized by using an oxidizing agent of hypohalogenite to form (aryl substituted)carboxylic acid and the reaction product is then refined by the hydrogen treatment of halogenated by-products contained in the aimed product of (aryl substituted)carboxylic acid.

(2) Description of the Prior Art

In connection with the method for preparing the (aryl substituted)carboxylic acid by oxidizing (aryl substituted)aldehyde, various oxidizing agents have been hitherto proposed. Among them, the methods using hypohalogenous acid or its salts as oxidizing agents, are regarded as preferable ones because their oxidizing efficiency is high. Methods of this kind are disclosed in the following references:

(a) In Japanese Laid-Open Patent Publication No. 53-18534 is disclosed a method for synthesizing 2-(p-isobutylphenyl)propionic acid as a medicine by oxidizing 2-(p-isobutylphenyl)propionaldehyde with hypohalogenite in the presence of acetic acid.

(b) In Japanese Laid-Open Patent Publication No. 55-2614 is disclosed a method for obtaining 2-(m-benzoylphenyl)propionic acid from 2-(m-arylphenyl)propionaldehyde by the oxidation with hypohalogenous acid. In a similar method disclosed in Japanese Laid-Open Patent Publication No. 56-113736, hypochlorite is used.

The present inventors have found the fact that the oxidation using hypohalogenite (hereinafter referred to as "oxidizing agent") excels in the oxidation efficiency but the generation of halogen molecules from the oxidizing agent cannot be avoided. In addition, it was also found that (aryl substituted)carboxylic acid is inevitably contaminated with halogenated by-products. The formation of these halogenated by-products is specific to the oxidation with this oxidizing agent, and yet, the analysis such as structural analysis of them is difficult owing to the diversity of them. The (aryl substituted)carboxylic acid is used in the fields in which high purity and high safety are required. In such the fields, the contamination with halogenated by-products even though its quantity is quite small, is not desirable for the product of (aryl substituted)carboxylic acid.

In order to eliminate impurities, recrystallization is generally adopted. However, it is well known that an aimed product also comes into the remained filtrate after the separation of precipitated crystals. The contamination with impurities like the halogenated by-products must be severely avoided, therefore, the quantity of an aimed product remained in the filtrate is increased on purpose to rise purity, which fact inevitably reduces the recovery rate of an aimed product.

BRIEF SUMMARY OF THE INVENTION

The inventors have found that dehalogenation of halogenated by-products can be easily attained when hydrogen treatment is carried out in the presence of a transition metal catalyst, thereby accomplishing the present invention.

It is, therefore, the primary object of the present invention to provide an improved method for producing highly pure, that is, substantially chlorine free (aryl substituted)carboxylic acid.

Another object of the present invention is to provide a method for effectively producing (aryl substituted)carboxylic acid.

In accordance with the present invention, the method for producing (aryl substituted)carboxylic acid or its salt comprises the steps of:

(I) oxidizing (aryl substituted)aldehyde in an acidic phase in the presence of hypohalogenite; and (II) bringing the oxidized product obtained in the preceding step into contact in a liquid phase with hydrogen in the presence of a catalyst of transition metal of the group VIII in the periodic table.

DETAILED DESCRIPTION OF INVENTION

The (aryl substituted)carboxylic acids obtained by the method of the present invention are those having 7 to 18 carbon atoms and an aryl substituent group.

In the case of (aryl substituted)carboxylic acids having 19 or more carbon atoms, the efficiency of dehalogenation is worse in the step (II) of the invention even under a basic condition, owing to the lack of solubility to water.

The aryl substituent groups are exemplified by lower alkyl-substituted phenyl groups such as a phenyl group, methylphenyl group, ethylphenyl group, dimethylphenyl group, propylphenyl group and butylphenyl group; alkoxy-substituted phenyl groups having an oxygen atom such as methoxy phenyl group, ethoxy phenyl group, propoxy phenyl group and butoxy phenyl group; and other substituted phenyl groups such as alkylphenoxyphenyl group and alkylbenzyl group, as well as substituted naphthyl groups such as methylnaphthyl group and methoxynaphthyl group. If any of these substituted aryl groups is introduced into the second position relative to the carboxyl group of a carboxylic acid, such carboxylic acid is desirable because the marked advantage of the present invention can be expected owing to the fact that the hydrogen atoms bonded to the carbon atom in a second position is active and is liable to suffer halogenation.

The 1-(aryl substituted)carboxylic acids are exemplified by substituted benzoic acids such as alkyl benzoic acid. The 2-(substituted substituted)carboxylic acids are exemplified by 2-(aryl substituted)acetic acid and 2-(aryl substituted)propionic acid. More particularly, the 2-(aryl substituted)acetic acid is exemplified by 2-(p-isobutylphenyl)acetic acid; and the 2-(aryl substituted)propionic acids are exemplified by 2-phenylpropionic acid, 2-(p-alkylphenyl)propionic acids such as 2-(p-isobutylphenyl)propionic acid, 2-(aryloxyphenyl)propionic acid such as 2-(m-phenoxyphenyl)propionic acid, 2-(arylcarbonylphenyl)propionic acid such as 2-(m-benzoylphenyl)propionic acid, and 2-(methoxynaphthyl)propionic acid such as 2-(6-methoxynaphthyl)propionic acid.

As the (aryl substituted)aldehyde of the starting material in the method of the present invention, those which are prepared by any of known methods can be employed as far as they can be converted into the above-mentioned (aryl substituted)carboxylic acid by oxidation of the formyl group contained in said aldehyde.

In the following passages, the manner for practically working each step of the invention will be described in more detail.

The hypohalogenites used in the Step (I) are any one of sodium hypochlorite, potassium hypochlorite, calcium hypochlorite, sodium hypobromite and potassium hypobromite. These hypohalogenites are used intact or in the form of their aqueous solutions. The use quantity of the hypohalogenite is not less than 0.9 mole, preferably more than 0.95 mole, per one mole of the (aryl substituted)aldehyde. There is no upper limit with regard to the use quantity. However, if a large excess of hypohalogenite is used, the quantity of impurity of halogenated by-product increases considerably, so that the use quantity is up to 2 moles per one mole of the aldehyde in practical viewpoint.

The inorganic acid used in the Step (I) to carry out the oxidation under acidic condition is an inorganic protonic acid such as sulfuric acid, phosphoric acid and hydrochloric acid. These acids can be also used in the form of a mixture of them. The use quantity of the inorganic acid is not specified so long as it suffices for acidifying the reaction system. It is generally sufficient that 0.1 mole or more of an inorganic acid is used with respect to one mole of the hypohalogenite. In the present invention, organic protonic acids such as acetic acid can be also used, however, the foregoing acids are preferable in view of purity.

During the oxidation in the Step (I), an inert solvent can be used, which must neither coagulate nor freeze and well dissolve (aryl substituted)aldehyde. Exemplified as such solvents are water miscible solvents of ketones such as acetone, methyl ethyl ketone and methyl isobutyl ketone; ethers such as tetrahydrofuran and dioxane; and monohydric or polyhydric alcohols such as methanol, ethanol and ethylene glycol. Besides them, water insoluble solvents of paraffins such as hexane, naphthenes such as cyclohexane, and aromatic hydrocarbons such as benzene, toluene and xylene can also be used. However, the water miscible solvents are desirable.

The Step (I) is carried out by adding the foregoing oxidizing agent to (aryl substituted)aldehyde that is cooled and dissolved or not dissolved in the above-mentioned solvent. With the temperature rise during the oxidation, especially in the oxidation for obtaining 2-(aryl substituted)carboxylic acid, the generation of substituted aryl ketone greatly increases because active hydrogen atoms exist on the carbon atoms in α-positions of both the substituted aryl group and carboxylic acid group and these active hydrogens are easily oxidized. Accordingly, the reaction temperature is desirably kept as low as possible. In practice, however, reaction temperatures in the range of −30° C. to 0° C. are sufficient.

After the process in Step (I), unreacted substances and by-products are removed, if necessary, from the reaction system to obtain an oxidation product, which is supplied to the next Step (II).

As the method for obtaining the oxidation product, for example, an aqueous solution of basic substance is firstly added to the reaction system to make the system alkaline and organic impurities and by-products are removed by, for example, solvent extraction, thereby recovering an oxidation product—this product contains mainly a salt of the (aryl substituted)carboxylic acid— that is dissolved in the aqueous phase. This oxidation product can be then fed to the Step (II). In this case, it is indifferent that the inorganic substances of halogenous salts mainly derived from the oxidizing agent is still dissolved in the aqueous phase.

As described later, because the Step (II) allows the existence of water under basic condition, it is possible to feed this aqueous phase intact to the Step (II). In another method, the oxidation product—(aryl substituted)carboxylic acid—is precipitated by making the aqueous phase neutral or acidic and the oxidation product is then extracted by an organic solvent, and the thus obtained solution can be fed to the Step (II). In still another method, the oxidation product is recovered by evaporating the organic solvent or by recrystallization and the obtained oxidation product is then fed to the Step (II).

As described above, the oxidation product obtained in the Step (I) contains much halogenated by-products. Accordingly, in the case that the oxidation product is refined by recrystallization to a high purity for the purpose of use, the recrystallization must be carried out such that the quantity of the aimed product remaining in the filtrate is increased on purpose. This is not desirable because the recovery rate of the aimed product is inevitably lowered with economical disadvantage. That is, even when the oxidation product of the Step (I) is refined, for example, by recrystallization before it is fed to the Step (II), recrystallization in a light degree is sufficient. In other words, it is not necessary to eliminate the halogenated by-products completely. Therefore, the material to be fed to the next Step (II) can be crude one.

According to the method of the present invention, the Step (II) is carried out in a liquid phase. When the oxidation product is in the form of an aqueous solution or an organic solvent solution that is recovered from the Step (I), it is used intact or by adding water or a proper solvent to the material. If the oxidation product recovered from the Step (I) is in the form of solid (aryl substituted)carboxylic acid or its salt, it is dissolved into a suitable organic solvent or water to make up a liquid phase.

As an organic solvent, any suitable one can be used as far as it does not hinder the hydrogen treatment and it can dissolve the (aryl substituted)carboxylic acid or its salt. In view of the removal of the solvent from the reaction system after the hydrogen treatment, the boiling point of the solvent is desirably low. The organic solvents are typically exemplified by paraffins such as n-hexane and n-heptane; cycloparaffins such as cyclohexane; alcohols such as methanol, ethanol and ethylene glycol; and ethers such as acetone, dioxane and tetrahydrofuran. These organic solvents can be used as a mixture of two or more kinds.

When a salt of (aryl substituted)carboxylic acid is used, water is necessary in order to dissolve it. In this case, an organic solvent can exist together with water.

The catalyst used in the hydrogen treatment of the Step (II) is metals of group VIII in the periodic table. Among them, platinum (Pt), rhodium (Rh) and palladium (Pd) are preferable because their efficiency is good. If they have hydrogenation activity, they can be in a metal form. Otherwise, they are supported on a carrier such as alumina, silica or silica-alumina, or they may be in the forms of transition metal compounds such as chlorides or acetates which are reducible under hydrogen treatment conditions.

The reaction temperature in the Step (II) is desirably in the range of 20° C. to 170° C. When temperature is lower than 20° C., the treatment time is unpractically long because of the low efficiency in dehalogenation. On the other hand, when the temperature is higher than 170° C., it is also undesirable because undesirable nuclear hydrogenation of aromatic nuclei of (aryl substituted)carboxylic acid is intense. The pressure in hydrogen treatment is not any substantial factor in the present invention. That is, the reaction can be done at any pressure at or above atmospheric pressure, which means that a suitable pressure can be selected according to the temperature of reaction so as to maintain the reaction system in a liquid phase. In practice, pressures up to 80 kg/cm$^2$ are preferable.

In the Step (II), it is desirable that the hydrogen treatment is carried out under a basic condition. That is, the halogen produced by dehalogenation is rapidly neutralized by the basic substance and is converted into inert halogenide, thereby preventing the produced halogen from the recombination of it with the dehalogenated product and the (aryl substituted)carboxylic acid. In this case, in order to cause the neutralization to proceed rapidly, the existence of liquid phase water is desirable so as to maintain the above basic substance in an aqueous solution. By the way, as the Step (I) is done in an acidic condition, it is necessary to add an excess basic substance in order to make the reaction system of the Step (II) basic.

As the basic substances for this purpose, there are exemplified by amines such as trimethylamine, triethylamine and tributylamine; alkali metal lower alcoholates such as sodium methoxide, potassium methoxide, sodium ethoxide and potassium ethoxide; as well as inorganic alkaline substances of alkali metal carbonates such as sodium carbonate, potassium carbonate, sodium hydrogencarbonate and potassium hydrogencarbonate. In practice, inorganic alkaline substances are preferable. The addition quantity of a basic substance is not especially limited as far as it is sufficient for neutralizing the (aryl substituted)propionic acid produced by the oxidation, the acid added in the Step (I) and the halogen produced by the dehalogenation and further for making the reaction system basic.

It is only necessary for water to exist in a liquid phase. The water miscible organic solvents of alcohols such as methanol, ethanol and ethylene glycol, ketones such as acetone, ethers such as dioxane and tetrahydofuran can coexist with water in a dissolved state.

The quantity of water is sufficient if it can dissolve the above basic substances and the (aryl substituted)propionic acid.

In accordance with the method of the invention as described above, highly pure (aryl substituted)propionic acid substantially containing no halogenated by-product can be obtained. Therefore, even when it is used in the field of medicine in which special refining is required, the recrystallization becomes easy and the recovery of crystalline product can be done effectively. In addition, in the method of the present invention, the halogenated by-products are converted into the aimed product of (aryl substituted)propionic acid by hydrogen treatment. Accordingly, a side effect can be obtained in that the component generally regarded as an impurity can be recovered as the aimed product itself.

After the reaction of the Step (II), carboxylic acid can be obtained through a know method.

More particularly, the catalyst is filtered off and the filtrate is made below pH 7 by adding an acid to precipitate the carboxylic acid. The precipitate that is obtained by filtration is then extracted with an organic solvent such as n-hexane and, by evaporating the solvent, the aimed highly pure carboxylic acid is obtained in a high yield.

If desired, it is possible to refine further the obtained carboxylic acid by recrystallization. For this recrystallization, one or a mixture of hitherto known organic solvents, for example, alcohols such as methanol and ethanol and lower paraffins such as hexane and heptane can be used. In the case that a water soluble solvent such as alcohol is used, a mixture with water can also be used in order to adjust the solubility to the carboxylic acid.

Because a highly pure product can be obtained according to the method of the present invention, even when recrystallization is applied, the operation can be done without difficulty, which provides an advantage of high yield in the recrystallization.

The present invention will be described in more detail with reference to several examples.

EXAMPLE 1

Oxidation Step; Step (I)

A reaction medium of 150 ml of acetone, 26.8 g of 2-phenylpropionaldehyde and 5 g of 35% hydrochloric acid were fed into a 500 ml flask equipped with a stirrer and it was cooled to $-15°$ C. Maintaining at $-15°$ C. with vigorous stirring, 125 g of 12% aqueous solution of sodium hypochlorite was added dropwise slowly. The dropwise addition was continued for 3 hours.

After the reaction, the reaction mixture was made alkaline by the addition of 30 g of 30% aqueous solution of sodium hydroxide and it was rinsed thrice with 50 ml of n-hexane so as to remove organic contents such as reaction material. After that, it was made acidic again by adding 24 g of 35% hydrochloric acid. In this procedure, there appeared a milky turbidity owing to the precipitation of the product of 2-phenylpropionic acid. Extraction of the product was done thrice by adding each 100 ml of n-hexane. Then, 29.1 g of light yellow solid substance was obtained by removing the n-hexane under reduced pressure.

In connection with the crystalline powder obtained above, chlorine content was determined, where its result was 2600 wt.ppm. According to analysis, the reaction yield as pure 2-phenylpropionic acid was 95.7 mole %.

Hydrogenation Step; Step (II)

To 130 g of 5% sodium hydroxide aqueous solution was dissolved 22. g of the solid substance that was obtained in the foregoing Oxidation Step. The solution was fed into an autoclave with a stirrer together with 1 g of palladium catalyst carried on activated carbon (2 wt. % in catalyst content). The pressure in the autoclave was raised to 10 kg/cm$^2$ and reaction was carried out for 5 hours at 50° C. with stirring. After the reaction, the palladium catalyst was removed by filtration and the filtrate was made acidic by the addition of 18 g of 35% hydrochloric acid. In the like manner as the Oxidizing Step, the precipitate was extracted with n-hexane to obtain 21.7 g of white crystals. The yield was 96% and the melting point was 27°-29° C.

The thus obtained crystals were subjected to chlorine analysis and the chlorine content was 8 wt.ppm. It was thus clarified that highly pure 2-phenylpropionic acid is effectively prepared.

EXAMPLE 2

A reaction medium of 150 ml of acetone, 38 g of 2-(p-isobutylphenyl)propionaldehyde and 5 g of 35% hydrochloric acid were fed into a 500 ml flask equipped with a stirrer and it was cooled to $-15°$ C. Maintaining at $-15°$ C. with vigorous stirring, 130 g of 12% aqueous solution of sodium hypochlorite was added dropwise slowly. The dropwise addition was continued for 3 hours.

After the reaction, the reaction mixture was made alkaline by the addition of 35 g of 30% aqueous solution of sodium hydroxide and it was rinsed thrice with 50 ml of n-hexane so as to remove organic contents such as reaction material. After that, it was fed into an autoclave with a stirrer together with 2 g of palladium catalyst carried on activated carbon (2.5 wt.% in catalyst content). The pressure in the autoclave was raised to 20 $kg/cm^2$ and reaction was carried out for 5 hours at 60° C. with stirring. After the reaction, the palladium catalyst was removed by filtration and the filtrate was made acidic by the addition of 29 g of 35% hydrochloric acid. In this procedure, there appeared a milky turbidity owing to the precipitation of the product of 2-(p-isobutylphenyl)propionic acid. Extraction of the product was repeated thrice by adding each 100 ml of n-hexane. Then, 40.1 g of white crystalline powder was obtained by removing the n-hexane under reduced pressure. The reaction yield was 97 mol % and melting point was 75°-77° C.

The thus obtained crystals were subjected to chlorine analysis and the chlorine content was 9 wt.ppm. It was thus clarified that highly pure 2-(p-isobutylphenyl)propionic acid is effectively prepared.

EXAMPLE 3

In the like manner as Example 1, each 0.2 mol of the following 2-(aryl substituted)propionic acids were used in experiments:
(I) 2-(m-phenyloxyphenyl)propionaldehyde
(II) 2-(m-benzoylphenyl)propionaldehyde
(III) 2-(m-dimethoxyphenylmethylphenyl)propionaldehyde (IV) 2-(6-methoxynaphthyl)propionaldehyde The results with regard to the obtained crystals are shown in the following Table 1.

TABLE 1

| Starting Aldehyde | Chlorine Content (ppm) After Oxidation | After Refining with Hydrogen | Melting Point or Else, after Refining with Hydrogen (°C.) |
|---|---|---|---|
| (I) | 1700 | 23 | 172–175 (b.pt, 0.5 mmHg) |
| (II) | 2000 | 18 | 93–96 |
| (III) | 1600 | 14 | 93–97 |
| (IV) | 1600 | 9 | 154–158 |

EXAMPLE 4

In the like manner as Example 1, 26.4 g of p-methylphenylacetaldehyde as an aldehyde and 2.3 g of sulfuric acid were used. The oxidation was done by using 125 g of 12% aqueous solution of sodium hypochlorite at temperatures of $-10°$ to $-12°$ C., which was followed by the hydrogenation to obtain p-methylphenylacetic acid.

The preparation of catalyst for the hydrogenation was as follows:

Alumina was immersed into an aqueous solution of chloroplatinic acid and water was removed under reduced pressure to obtain a catalyst (catalyst content: 2.5%). It was then treated in a flow of hydrogen at 450° C. for 3 hours.

| Results of Oxidation Reaction: | |
|---|---|
| Yield: | 94% |
| Chlorine Content: | 1920 ppm |
| Results after Refining: | |
| Recovery Rate: | 93% |
| Chlorine Content: | 14 ppm |
| Melting Point: | 90–92° C. |

EXAMPLE 5

In the like manner as Example 1, 23.6 g of p-methylbenzaldehyde as an aldehyde and 3 g of phosphoric acid were used. The oxidation was done by using 23 g of calcium hypochlorite at temperatures of $-5°$ to $-3°$ C., which was followed by refining to obtain p-methylbenzoic acid.

The preparation of catalyst for the hydrogenation was as follows:

Asbestos was soaked with an aqueous solution of rhodium chloride and it was then reduced by immersing it into a mixed aqueous solution of formaldehyde and sodium hydroxide to obtain a catalyst (catalyst content: 3%).

| Results of Oxidation Reaction: | |
|---|---|
| Yield: | 92% |
| Chlorine Content: | 1200 ppm |
| Results after Refining: | |
| Recovery Rate: | 95% |
| Chlorine Content: | 17 ppm |
| Melting Point: | 173–176° C. |

EXAMPLE 6

In the like manner as Example 1, 23.6 g of p-methylbenzaldehyde as an aldehyde and 2.3 g of sulfuric acid were used. The oxidation was done by using 125 g of 12% aqueous solution of sodium hypochlorite at temperature of $-5°$ to $2°$ C., which was followed by the hydrogenation.

| Results of Oxidation Reaction: | |
|---|---|
| Yield: | 98% |
| Chlorine Content: | 2100 ppm |
| Results after Refining: | |
| Recovery Rate: | 93% |
| Chlorine Content: | 13 ppm |
| Melting Point: | 174–176° C. |

COMPARATIVE EXAMPLE 1

The light yellow crystals of 2-phenylpropionic acid (5 g) prepared in Oxidation Step of Example 1 were dissolved into 15 g of n-hexane by heating. After that, the solution was cooled by allowing it to stand so as to precipitate crystals. It was then filtered during cool and n-hexane was removed under reduced pressure to obtain white crystals. The chlorine contents remained in the thus obtained crystals were analyzed, the results of which are shown in the following Table 2.

TABLE 2

| | Chlorine Content in 2-Phenylpropionic Acid | | |
|---|---|---|---|
| Yield (g) | Recovery (%) | Chlorine Content (ppm) | Melting Point (°C.) |
| 1.2 | 24 | 490 | 27–29 |
| 2.4 | 48 | 670 | — |
| 3.6 | 72 | 1700 | — |
| 4.1 | 82 | 1800 | 24–26 |

COMPARATIVE EXAMPLE 2

In the like manner as (Oxidation Step) of Example 1, light yellow crystals of 2-(p-isobutylphenyl)propionic acid were prepared from the reaction mixture obtained after the oxidation step of Example 2. The crystalline product was subjected to recrystallization in the like manner as Comparative Example 1 and the chlorine contents remained in the thus obtained crystals were analyzed, the results of which are shown in the following Table 3.

TABLE 3

| | Chlorine Content in 2-(p-Isobutylphenyl)propionic Acid | | |
|---|---|---|---|
| Yield (g) | Recovery (%) | Chlorine Content (ppm) | Melting Point (°C.) |
| 1.3 | 46 | 210 | 75–77 |
| 2.6 | 52 | 760 | — |
| 3.2 | 64 | 2200 | — |
| 3.8 | 76 | 2500 | 72–76 |

EXAMPLE 7

In the like manner as (Oxidation Step) of Example 1, light yellow crystals of 2-(p-isobutylphenyl)propionic acid (chlorine content: 2800 ppm) were prepared from the reaction mixture obtained after the oxidation step of Example 2. 2.5 g of the crystalline product was dissolved into 30 ml of n-hexane and it was fed into a 200 ml autoclave equipped with a stirrer, together with 0.13 g of palladium catalyst (catalyst content: 5 wt. %) carried on activated carbon. Reaction was continued for 9 hours at 60° C. and at 10 kg/cm$^2$ of hydrogen pressure. After the reaction, the palladium catalyst was removed by filtration and n-hexane was removed under reduced pressure to obtain 2-(p-isobutylphenyl)propionic acid. The recovery rate was 96% and the chlorine content was 65 ppm.

As described above, highly pure (aryl substituted)carboxylic acid can be prepared effectively by applying the method of the present invention to the production process of the same.

EXAMPLE 8

Oxidation Step; Step (I)

This step was carried out in the like manner as the foregoing Example 1 except that the reaction mixture obtained after the reaction was supplied to the next Step (II) as it stands in basic.

In the experiment, a reaction medium of 150 ml of acetone, 26.8 g of 2-phenylpropionaldehyde and 5 g of 35% hydrochloric acid were fed into a 500 ml flask equipped with a stirrer and it was cooled to −15° C. Maintaining at −15° C. with vigorous stirring, 125 g of 12% aqueous solution of sodium hypochlorite was added dropwise slowly. The dropwise addition was continued for 3 hours.

After the reaction, the reaction mixture was made alkaline by the addition of 30 g of 30% aqueous solution of sodium hydroxide and it was rinsed thrice with 50 ml of n-hexane so as to remove organic contents such as reaction material.

Hydrogenation Step; Step (II)

The alkaline solution that was obtained in the above Step (I) was fed into an autoclave with a stirrer together with 1 g of palladium catalyst carried on activated carbon (2 wt. % in catalyst content). The pressure in the autoclave was raised to 10 kg/cm$^2$ and reaction was carried out for 8 hours at 50° C. with stirring. After the reaction, the palladium catalyst was removed by filtration and, in the like manner as Example 1, the filtrate was made acidic again by the addition of 24 g of 35% hydrochloric acid, liberating the product of 2-phenylpropionic acid as a milky precipitate. In the like manner as the Step (I) of Example 1, the product was extracted three times with each 100 ml of n-hexane and n-hexane was evaporated under reduced pressure to obtain 28.9 g of white crystals. The overall reaction yield from the Step (I) was 96.3 mol % as pure 2-phenylpropionic acid, and the melting point of the crystals was 27°–29° C. and chlorine content, 8 wt ppm.

It will be understood from the foregoing examples that highly pure 2-phenylpropionic acid is obtained in a high yield by carrying out the Step (II) of the present invention in addition to the Step (I).

The fact that the highly pure 2-phenylpropionic acid can be obtained in a high yield by adding the Step (II) to the Step (I) was firstly found out by the inventors of the present invention.

What is claimed is:

1. A method for producing highly pure (aryl substituted)carboxylic acid or its salt which comprises the steps of:
    (I) oxidizing (aryl substituted)aldehyde in an acidic phase in the presence of hypohalogenite; and
    (II) bringing the oxidized product obtained in the preceding step into contact in a liquid phase with hydrogen in the presence of a catalyst of transition metal of the group VIII in the periodic table.

2. The method for producing (aryl substituted)carboxylic acid or its salt in claim 1, wherein the acidic phase in said Step (I) is made up by using at least one member selected from the group of inorganic acids consisting of sulfuric acid, phosphoric acid and hydrochloric acid.

3. The method for producing (aryl substituted)carboxylic acid or its salt in claim 1, wherein said hypohalogenite in said Step (I) is at least one member selected from the group consisting of sodium hypochlorite, potassium hypochlorite, calcium hypochlorite, sodium hypobromite, and potassium hypobromite.

4. The method for producing (aryl substituted)carboxylic acid or its salt in claim 1, wherein said catalyst of transition metal of group VIII in the periodic table is at least one member selected from the group consisting of palladium, rhodium and platinum.

5. The method for producing (aryl substituted)carboxylic acid or its salt in claim 1, wherein said (aryl substituted)carboxylic acid is any one of 1-(aryl substituted)carboxylic acid and 2-(aryl substituted)carboxylic acid.

6. The method for producing (aryl substituted)carboxylic acid or its salt in claim 5, wherein said 1-(aryl substituted)carboxylic acid is substituted benzoic acid.

7. The method for producing (aryl substituted)carboxylic acid or its salt in claim 5, wherein said 2-(aryl substituted)carboxylic acid is 2-(aryl substituted)acetic acid or 2-(aryl substituted)propionic acid.

8. The method for producing (aryl substituted)carboxylic acid or its salt in claim 7, wherein said 2-(aryl substituted)propionic acid is at least one member selected from the group consisting of 2-phenylpropionic acid, 2-(alkylphenyl)propionic acid, 2-(aryloxyphenyl)propionic acid, 2-(arylcarbonylphenyl)propionic acid, and 2-(methoxynaphthyl)propionic acid.

9. The method for producing (aryl substituted)carboxylic acid or its salt in claim 7, wherein said 2-(aryl substituted)propionic acid is at least one member selected from the group consisting of 2-(p-isobutylphenyl)propionic acid, 2-(m-phenoxyphenyl)propionic acid, 2-(m-benzoylphenyl)propionic acid, and 2-(6-methoxynaphthyl)propionic acid.

10. The method for producing (aryl substituted)carboxylic acid or its salt in claim 1, wherein said Step (II) is carried out under a basic condition.

11. The method for producing (aryl substituted)carboxylic acid or its salt in claim 1, wherein said Step (II) is carried out in a liquid phase in the presence of water.

12. The method for producing (aryl substituted)carboxylic acid or its salt in claim 1, wherein said Step (II) is carried out at reaction temperatures in the range of 20° C. to 170° C..

13. The method for producing (aryl substituted)carboxylic acid or its salt in claim 10, wherein said basic condition is made up by using at least one member selected from the group consisting of amines, metal lower alcoholates and inorganic alkaline substances.

14. The method for producing (aryl substituted)carboxylic acid or its salt in any one of claims 1 to 13, wherein the salt of 2-(aryl substituted)propionic acid which is obtained by the contact with hydrogen, is recovered in a free acid form by acidifying below pH 7 with the addition of an acid.

* * * * *

UNITED STATES PATENT AND TRADEMARK OFFICE
CERTIFICATE OF CORRECTION

PATENT NO. : 4,814,494

DATED : March 21, 1989

INVENTOR(S) : Isoo Shimizu, et al.

It is certified that error appears in the above-identified patent and that said Letters Patent is hereby corrected as shown below:

Column 6, line 56: "22. g of the" should read as --22.5 g of the--

Signed and Sealed this

Twenty-third Day of January, 1990

Attest:

JEFFREY M. SAMUELS

Attesting Officer     Acting Commissioner of Patents and Trademarks